United States Patent
Chan et al.

(10) Patent No.: US 9,456,648 B2
(45) Date of Patent: Oct. 4, 2016

(54) SYSTEMS AND METHODS FOR HELMET LINER EVALUATION

(71) Applicant: Elwha LLC, Bellevue, WA (US)

(72) Inventors: Alistair K. Chan, Bainbridge Island, WA (US); Geoffrey F. Deane, Bellevue, WA (US); William D. Duncan, Mill Creek, WA (US); Philip A. Eckhoff, Kirkland, WA (US); Bran Ferren, Beverly Hills, CA (US); William Gates, Medina, WA (US); W. Daniel Hillis, Encino, CA (US); Roderick A. Hyde, Redmond, WA (US); Muriel Y. Ishikawa, Livermore, CA (US); Edward K. Y. Jung, Bellevue, WA (US); Jordin T. Kare, San Jose, CA (US); John Latham, Boulder, CO (US); Max N. Mankin, Cambridge, MA (US); Nathan P. Myhrvold, Medina, WA (US); Robert C. Petroski, Seattle, WA (US); Clarence T. Tegreene, Mercer Island, WA (US); David B. Tuckerman, Lafayette, CA (US); Thomas A. Weaver, San Mateo, CA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 14/600,516

(22) Filed: Jan. 20, 2015

(65) Prior Publication Data

US 2016/0206033 A1 Jul. 21, 2016

(51) Int. Cl.
| G01M 7/00 | (2006.01) |
| A42B 3/04 | (2006.01) |
| A42B 3/12 | (2006.01) |
| G01N 3/30 | (2006.01) |
| G01N 33/00 | (2006.01) |

(52) U.S. Cl.
CPC ............... *A42B 3/0433* (2013.01); *A42B 3/12* (2013.01); *G01N 3/30* (2013.01); *G01N 2033/0086* (2013.01)

(58) Field of Classification Search
CPC .... A42B 3/046; A42B 3/0433; A42B 3/068; G01N 2033/0086; G01N 3/30
USPC .............................................. 73/12.04, 12.09
See application file for complete search history.

(56) References Cited

U.S. PATENT DOCUMENTS

| 5,847,976 | A | * | 12/1998 | Lescourret | ............. G01S 1/022 324/207.13 |
| 5,978,972 | A | | 11/1999 | Stewart et al. | |
| 6,065,158 | A | | 5/2000 | Rush, III | |
| 6,301,718 | B1 | | 10/2001 | Rigal | |
| 6,332,226 | B1 | | 12/2001 | Rush, III | |
| 6,704,943 | B2 | | 3/2004 | Calonge Clavell | |
| 7,509,835 | B2 | * | 3/2009 | Beck | ..................... A42B 3/046 2/425 |
| 8,157,402 | B2 | * | 4/2012 | Huss | ................... A42B 3/0433 362/103 |

(Continued)

*Primary Examiner* — Max Noori
(74) *Attorney, Agent, or Firm* — Foley & Lardner LLP

(57) ABSTRACT

A helmet testing apparatus including a movable member, a sensor coupled to the movable member and configured to acquire compliance data regarding a liner disposed within a shell of a helmet through engagement of the sensor with the liner, and a processing circuit configured to determine a rating for the helmet based on the compliance data and predetermined compliance parameters for the helmet.

34 Claims, 6 Drawing Sheets

(56) References Cited

U.S. PATENT DOCUMENTS

| | | | |
|---|---|---|---|
| 2004/0074283 A1* | 4/2004 | Withnall | G01N 3/32 73/12.12 |
| 2007/0089480 A1 | 4/2007 | Beck | |
| 2008/0256685 A1* | 10/2008 | Lampe | A42B 3/068 2/411 |
| 2011/0117310 A1 | 5/2011 | Anderson et al. | |
| 2012/0126803 A1 | 5/2012 | Goldfine et al. | |
| 2012/0247178 A1* | 10/2012 | Kis, Jr. | G01N 3/30 73/12.04 |
| 2013/0312161 A1 | 11/2013 | Anderson et al. | |
| 2013/0340147 A1 | 12/2013 | Giles | |

* cited by examiner

SYSTEMS AND METHODS FOR HELMET LINER EVALUATION

BACKGROUND

Over time (e.g., a certain number of impacts, plays, time of use, etc.), liners of head protection devices such as helmets may begin to degrade due to impacts or other forces (e.g., weather, extended use, etc.). As a result of the degradation of the liner, the performance of the helmet in reducing the forces and accelerations from impacts to a user's head may begin to diminish.

SUMMARY

One embodiment relates to a helmet testing apparatus. The helmet testing apparatus includes a movable member, a sensor coupled to the movable member and configured to acquire compliance data regarding a liner disposed within a shell of a helmet through engagement of the sensor with the liner, and a processing circuit configured to determine a rating for the helmet based on the compliance data and predetermined compliance parameters for the helmet.

Another embodiment relates to a testing apparatus. The testing apparatus includes a memory configured to store a first set of testing data regarding a condition of a liner of a helmet at a first point in time, a sensor configured to acquire a second set of testing data regarding the condition of the liner at a second later point in time, and a processing circuit configured to determine a rating for the helmet based on a comparison of the first and second sets of testing data regarding the condition of the liner.

Another embodiment relates to a helmet. The helmet includes a shell, a liner disposed within the shell, a processing circuit configured to determine a required test inspection time for the helmet, and an indicator module configured to provide an indication of the required test inspection time for the helmet.

Another embodiment relates to a method of testing a helmet. The method of testing a helmet includes providing the helmet including a shell with a liner disposed within the shell, coupling the helmet to a test device including a sensor, selectively positioning the sensor to engage a portion of the liner to acquire compliance data regarding the liner, and determining, by a processing circuit, a rating for the helmet based on the compliance data and predetermined compliance parameters for the helmet.

Another embodiment relates to a method of testing a helmet. The method of testing a helmet includes storing, in a memory, a first set of testing data regarding a condition of a liner of a helmet at a first point in time, acquiring, by a sensor, a second set of testing data regarding the condition of the liner at a second later point in time, and determining, by a processing circuit, a rating for the helmet based on a comparison of the first and second sets of testing data regarding the condition of the liner.

Another embodiment relates to a method of determining a test time for a helmet. The method of determining a test time for a helmet includes determining, by a controller, a required test inspection time for a liner disposed within a shell of the helmet and providing, by an indicator module coupled to the shell of the helmet, an indication of the required test inspection time for the liner.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1:
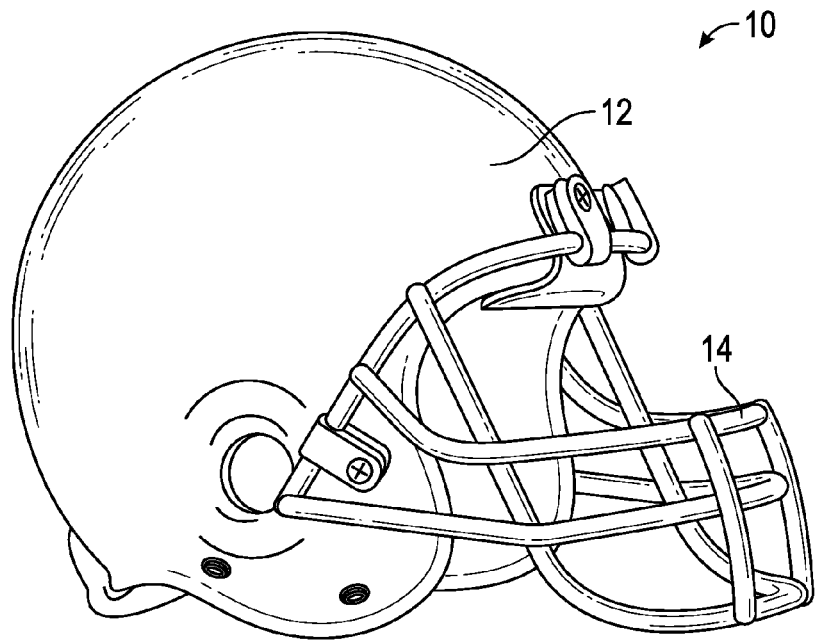
FIG. 1 is a perspective view of a helmet according to one embodiment.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the Figures generally, various embodiments disclosed herein relate to a helmet testing apparatus which measures the compliance of an interior liner of a helmet (e.g., a head protection assembly such as a football helmet, hockey helmet, motorcycle helmet, motocross helmet, etc.) for users such as athletes, motor vehicle operators, and the like. In some embodiments, the compliance (e.g., cushioning, dampening, etc.) of the interior liner of the helmet may be checked for deflection, strain rate performance, angular momentum dampening, discoloration, or other compliance indicators. In further embodiments, the compliance of the outer shell of the helmet may be checked (e.g., cracks, dents, etc.). The compliance of the helmet may be compared to a standard operating performance (e.g., average compliance, etc.) of functioning helmets (e.g., new helmets, helmets without any damage, etc.). The compliance of the helmet liners may also be tracked over time, determining a rate of degradation of the liner to predict when maintenance or replacement of the liner may be necessary.

Figure 2:
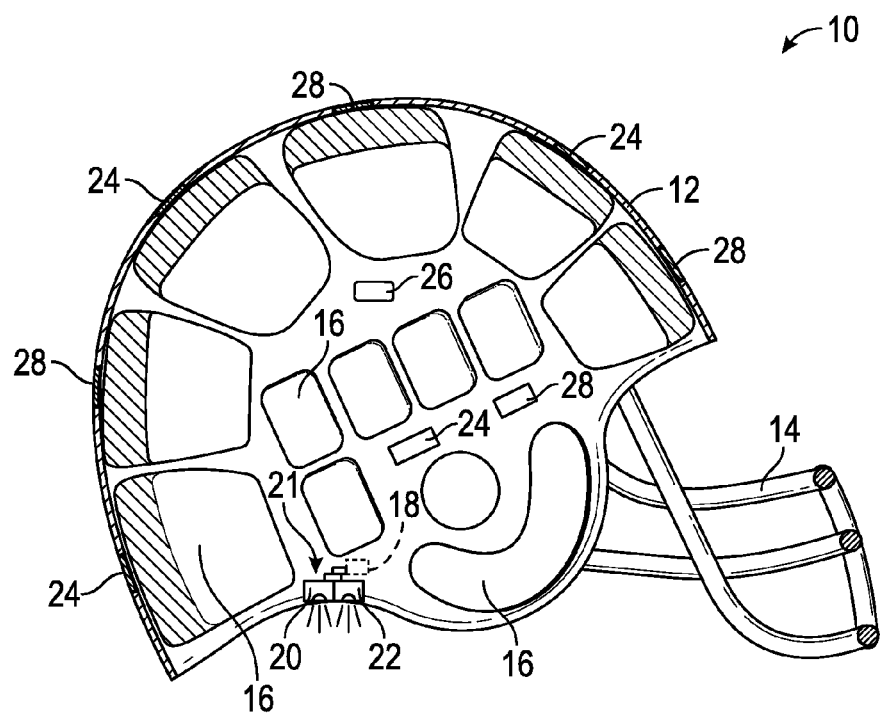
FIG. 2 is a cross-sectional view of the helmet of FIG. 1 according to one embodiment.

Referring now to FIGS. 1-2, a helmet, shown as helmet 10, is shown according to one embodiment. Helmet 10 is usable to reduce the risk of injury to users while performing various activities, including playing sports (e.g., football, hockey, etc.) and operating motor vehicles (e.g., motorcycles, snowmobiles, ATVs, etc.). In the example embodiment, helmet 10 is a football helmet. In other embodiments, helmet 10 may be any helmet used to protect a user from impacts to the head (e.g., during activities such as motocross, snowboarding, hockey, lacrosse, snowmobiling, etc.). As shown in FIG. 1, helmet 10 includes a shell, shown as shell 12, and a face protection device, shown as facemask 14. Shell 12 may be structured as any type of helmet shell (e.g., football, baseball, hockey, motocross, etc.) used to protect a user's head. Facemask 14 may be any type of helmet facemask to protect the user's face. In some embodiments, facemask 14 may include one or more crossbars, a transparent shield, or other protection devices. In yet further embodiments, facemask 14 may be rigidly attached to shell 12, forming a single continuous unitary outer shell (e.g., a motocross helmet, etc.), or removably attached (i.e., detachable) to shell 12 (e.g., a hockey helmet, a football helmet, etc.). In yet further embodiments, facemask 14 is omitted (e.g., a baseball helmet, etc.).

As shown in FIG. 2, the interior of helmet 10 includes a helmet liner and pads, shown as liner 16. Liner 16 may be any type of helmet padding (e.g., foam padding, inflatable pads, webbing, etc.) for added head protection to the user of helmet 10. Also within the interior of helmet 10, helmet 10 includes an indicator module 21 which includes controller 18, indicators, shown as first indicator 20 and second indicator 22, data markings 26, and sensors, shown as helmet sensors 24 or scheduling sensors 28. Helmet sensors 24, scheduling sensors 28, indicator module 21, and data markings 26 are shown to be disposed on shell 12. In other embodiments, these may be distributed about a portion of shell 12, facemask 14, liner 16, and/or any other location of helmet 10.

Helmet 10 is configured to reduce impact forces, torques, and accelerations to the head of a user in cases of impacts or collisions to the user's head (e.g., such as collisions between players during a sporting activity, collisions between a motor vehicle operator and other motor vehicles or operators, etc.). Helmet sensors 24 are configured to measure impact data (e.g., at least one of impact forces, torques, accelerations, etc.) regarding an impact to helmet 10. Indicator module 21 is configured to provide an indication when the impact data exceeds an impact threshold. For example, after a substantial impact (e.g., substantial force, acceleration, torque, etc.) to helmet 10 (i.e., a user's head, neck, etc.) is measured by helmet sensors 24 which exceeds the impact threshold, helmet 10 may provide an indication that required testing needs to be run on helmet 10 to check for damage and/or the user to check for injury (e.g., concussion, neck injury, etc.). The indication may include a change in the profile of helmet 10 (e.g., due to deformations resulting from impacts, etc.), an audible indication (e.g., a sound, a tone, an alarm, etc.), a visual indication (e.g., a light, a flashing light, smoke, etc.), and/or a transmission of a wireless communication to a remote device (e.g., a remote server, laptop, tablet, smartphone, etc.). The audible indication and the visual indication may be triggered by controller 18 via at least one of first indicator 20 and second indicator 22. The transmission of the wireless communication may be sent by controller 18 to a remote device to notify an equipment manager, the user, a coach, an official, a doctor, or any other person deemed necessary. In some embodiments, the transmission of the wireless communication is sent based on a schedule or an event (e.g., upon the taking or analysis of sensor data). In other embodiments, transmission of the wireless communication is performed by an RFID tag (active or passive) upon receipt of a query from a remote device (e.g., an RFID reader).

Figure 3:
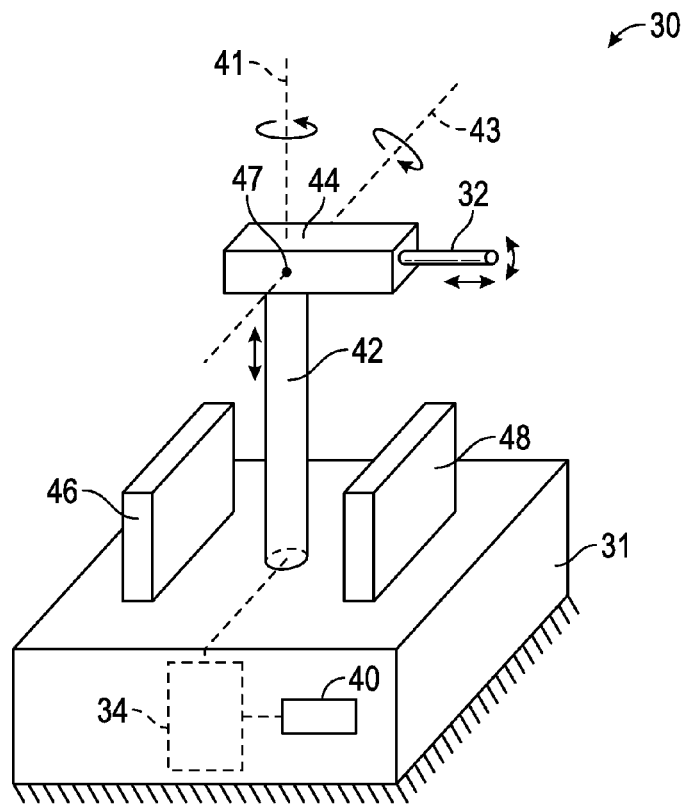
FIG. 3 is a schematic illustration of a test device for testing the helmet of FIG. 1 according to one embodiment.

Referring now to FIGS. 3-6, a helmet testing apparatus, shown as test device 30, is shown. As shown in FIG. 3, test device 30 includes a base member, shown as base 31, a first moveable member, shown as first motion control shaft 42, a second moveable member, shown as second motion control shaft 44, and a sensor, shown as sensor 32. Base 31 provides a base structure for test device 30. A bottom surface of base 31 rests atop a supporting surface (e.g., a table, a counter, a ground surface, etc.). A first end (e.g., base end, bottom end, proximal end, etc.) of first motion control shaft 42 rotatably couples to base 31 and defines a vertical axis, shown as vertical axis 41. A first end (e.g., connection end, rotation end, non-sensor end, etc.) of second motion control shaft 44 is rotatably coupled to a second end (e.g., distal end, top end, etc.) of first motion control shaft 42 via a pin, shown as pin 47. Pin 47 defines a lateral axis, shown as lateral axis 43. Sensor 32 is disposed at a second end (e.g., sensor end, distal end, etc.) of second motion control shaft 44. Support members, shown as first support member 46 and second support member 48, are disposed along the top surface of base 31, on opposing sides of first motion control shaft 42, and are configured to support helmet 10 during testing. In another embodiment (not shown), sensor 32 is mounted in a fixed configuration, and the helmet is mounted to a movable member which rotates and/or translates the helmet relative to the location of sensor 32. In other embodiments, both sensor 32 and the helmet are mounted to movable members; for example, the helmet undergoes one-dimensional horizontal rotation about a vertical axis, while sensor 32 undergoes vertical motion and/or pitch rotation.

Figure 4:
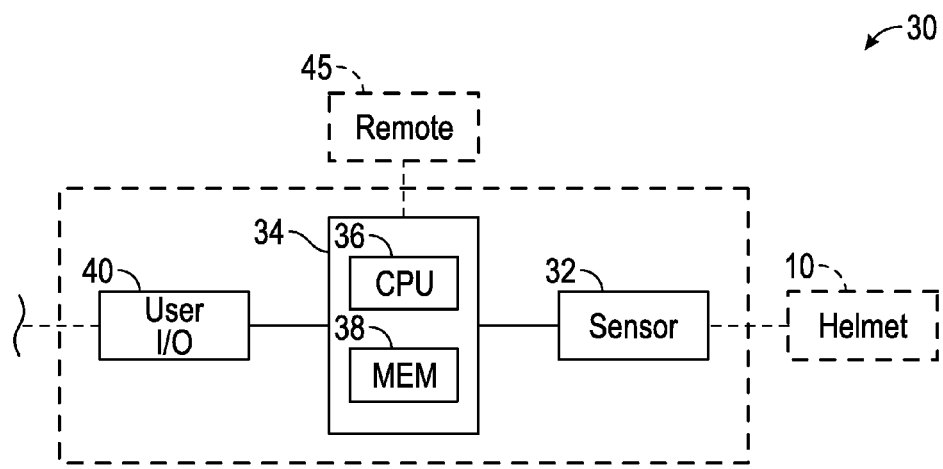
FIG. 4 is a schematic block diagram of the test device of FIG. 3 according to one embodiment.

As shown in FIGS. 3-4, test device 30 includes processing circuit 34. Processing circuit 34 includes processor 36 and memory 38. Processor 36 may be implemented as a general-purpose processor, an application specific integrated circuit (ASIC), one or more field programmable gate arrays (FPGAs), a digital-signal-processor (DSP), a group of processing components, or other suitable electronic processing components. Memory 38 is one or more devices (e.g., RAM, ROM, Flash Memory, hard disk storage, etc.) for storing data and/or computer code for facilitating the various processes described herein. Memory 38 may be or include non-transient volatile memory or non-volatile memory. Memory 38 may include database components, object code components, script components, or any other type of information structure for supporting the various activities and information structures described herein. Memory 38 may be communicably connected to processor 36 and provide computer code or instructions to processor 36 for executing the processes described herein.

Referring still to FIGS. 3-4, test device 30 includes user input/output (I/O) device 40. As shown in FIGS. 3-4, user I/O device 40 is communicably coupled to processing circuit 34, such that information may be exchanged between processing circuit 34 and user I/O device 40, wherein the information may relate to one or more components of test device 30. User I/O device 40 enables an operator of the test device 30 to communicate with processing circuit 34 and one or more components of test device 30. In some embodiments, user I/O device 40 may include, but is not limited to, an interactive display, a touchscreen device, one or more buttons and switches, voice command receivers, etc. In other embodiments, user I/O device 40 may include a laptop computer, a tablet computer, a desktop computer, a phone, a watch, a personal digital assistant, etc. As shown in FIG. 4, sensor 32 is communicably coupled to processing circuit 34, such that information (e.g., compliance data, movement commands, etc.) may be exchanged between processing circuit 34 and sensor 32.

Figure 5:
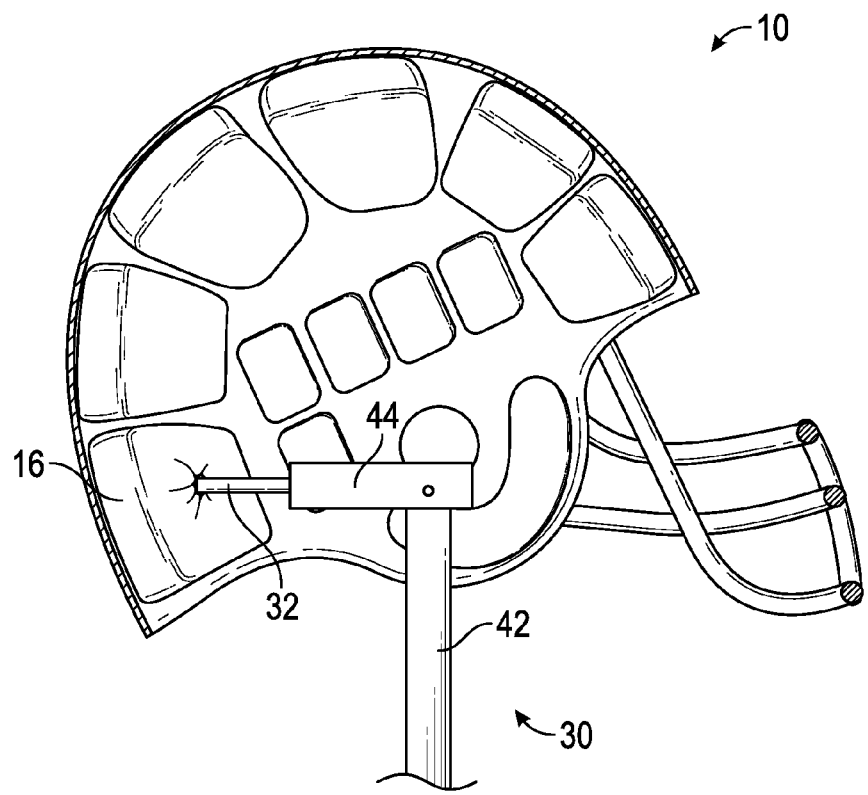
FIG. 5 is an illustration of a test device testing a helmet according to one embodiment.
Figure 6:
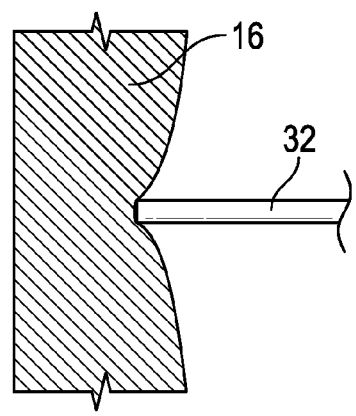
FIG. 6 is an illustration of a test device testing a portion of a helmet according to another embodiment.

As shown in FIGS. 5-6, test device 30 may interact with liner 16 of helmet 10. By way of example, opposing lateral sides of helmet 10 may rest on first support member 46 and second support member 48 (see, e.g., FIG. 3). When resting on first support member 46 and second support member 48, the interior of helmet 10 encloses first motion control shaft 42, second motion control shaft 44, and sensor 32 of test device 30, as shown in FIG. 5. As shown in FIG. 3, first motion control shaft 42 may extend and retract along vertical axis 41, as well as rotate about vertical axis 41. Second motion control shaft 44 may rotate about lateral axis 43. Sensor 32 may extend from or retract into second motion control shaft 44, as well as rotate about the connection point between the second motion control shaft 44 and sensor 32. Thereby, test device 30 may selectively position sensor 32 to engage (e.g., contact, analyze, etc.) any portion of the interior of helmet 10 to acquire compliance data regarding liner 16. The position of sensor 32 may be chosen by a user of test device 30 via user I/O device 40 or by processing circuit 34 (e.g., a preset program stored in memory 38 and accessed by processor 36, etc.).

As mentioned above, helmet 10 is configured to reduce impact forces, torques, and accelerations to the head of a user. Over time (e.g., a certain number of impacts, plays, time of use, etc.), liner 16 of helmet 10 may begin to degrade from such impacts or other degrading forces (e.g., weather, extended use, etc.). Throughout the degradation of liner 16, the performance of helmet 10 to reduce the forces and accelerations from impacts to the user's head may begin to diminish, putting the user in greater risk of sustaining injuries (e.g., concussions, etc.). Test device 30 may be used to quantify the compliance of liner 16 of helmet 10 by comparing the compliance of liner 16 with certain standards or regulations (e.g., of a certain league, of a law, of a manufacturer, etc.) to determine a rating for helmet 10. The frequency of testing the compliance of liner 16 may be based on a schedule (e.g., number of days, time-in-use, number of plays, number of impacts, etc.). In the context of a helmet used in sports (e.g., football, etc.), the testing may be done between plays, during timeouts, or other breaks in play on the sideline, in an equipment room between games, or other chosen locations. Helmet 10 (e.g., indicator module 21, etc.) may report when it is due (or overdue) for inspection via communication to a remote device (e.g., via controller 18, etc.) or a visual and/or auditory indication (e.g., via indicators 20 and 22, etc.).

As shown in FIGS. 5-6, sensor 32 is configured as a contact sensor. The contact sensor may be a touch probe, contact profilometer (e.g., touch, capacitive, etc.), or another type of contact sensor (e.g., pressure sensor, strain gauge, etc.). Sensor 32 may be selectively positioned into a plurality of locations to engage and measure the compliance of liner 16 at the plurality of locations. Sensor 32 may measure at least one of a radial compliance and an azimuthal compliance of liner 16. In one embodiment, sensor 32 is configured to test the plurality of locations of liner 16 in a serial manner (e.g., one at a time, etc.). In other embodiments, the test device 30 may include a plurality of sensors, like sensor 32, configured to test a plurality of locations simultaneously (see, e.g., FIG. 7). In one embodiment, the plurality of locations may be defined by a one-dimensional grid extending along liner 16. For example, liner 16 may be divided by a series of one-dimensional grids extending along the circumference of helmet 10 at varying locations along vertical axis 41. Therefore, test device 30 may measure the compliance of liner 16 along a first line (e.g., a first one-dimensional grid, etc.) around the circumference of helmet 10. The first motion control shaft 42 may then extend along vertical axis 41, moving sensor 32 further into the interior of helmet 10. Next, test device 30 may measure the compliance of liner 16 along a second line (e.g., a second one-dimensional grid, etc.) around the circumference of helmet 10. In another embodiment, the plurality of locations may be defined by a two-dimensional grid disposed about liner 16. For example, test device 30 may focus on a certain area of liner 16 by having sensor 32 measure the compliance about the selected area. In this example, the test device 30 may determine if a portion of liner 16 is dented or missing. In another embodiment, the plurality of locations may be defined by physical features of the liner. For example, the liner may be composed of discrete, spaced apart, pads; the test device 30 may focus on the discrete pads and avoid the spaces in between them. In another example, the physical features may comprise discoloration of a portion of the liner (e.g., due to water damage); the test device 30 may focus on the discolored region. In some embodiments, the location of the physical features may be predefined (e.g., the layout of discrete pads). In some embodiments, a sensor such as a camera may be used to image the interior of the helmet so as to identify the presence and location of physical features of the liner. In other embodiments, the plurality of locations may also be defined by corresponding locations of anatomical features (e.g., ears, temple, forehead, nape, crown, jaw, etc.) of a user of helmet 10. The plurality of locations may be selected based on previous compliance test data regarding the helmet. For example, in a prior compliance test (e.g., a first compliance test, an first point in time, an earlier point in time, etc.) which discovered substantial degradation in certain areas, the current test (e.g., a second later compliance test, a second later point in time, etc.) may focus on those areas to check if the degradation has continued and the rate at which the degradation is occurring.

Referring further to FIGS. 5-6, at each of the plurality of locations, sensor 32 may test a linear and/or a nonlinear response of liner 16 by deforming liner 16 with one of a steady load (e.g., constant, linear, etc.) to acquire compliance data (e.g., deflection, dampening, etc.) or a pulsed load (e.g., varying, sinusoidal, square wave, etc.) to acquire compliance data (e.g., strain rate performance, etc.). The compliance data may also be correlated with environmental conditions such as temperature, humidity, and other environmental conditions that may affect the compliance of liner 16. As mentioned above, sensor 32 and processing circuit 34 are communicably coupled such that the acquired compliance data may be received by processing circuit 34. Processing circuit 34 is configured to determine a rating for helmet 10 based on the compliance data acquired by sensor 32 and predetermined compliance parameters (e.g., compliance standards, regulations, etc. for helmet 10 and/or liner 16) stored in memory 38 or elsewhere. Processing circuit 34 may also be configured to determine the rating based on the linear or nonlinear response of liner 16. The rating may further be based on at least one of environmental conditions, a time since a previous test, a time-in-use, a number of uses (e.g., number of plays, number of times the helmet is worn, etc.), and any other use characteristics (e.g., number of collisions, etc.) of helmet 10.

The rating of helmet 10 includes one or more of an indication of whether helmet 10 is suitable for use, is not suitable for use, requires maintenance, or requires further inspection (e.g., by an equipment manager, the manufacturer, etc.). In some embodiments, the rating includes a degree of degradation. Processing circuit 34 may determine a degree of degradation of liner 16 relative to a predetermined degradation threshold (e.g., maximum allowable degradation of liner 16 before helmet 10 may no longer be used with the current liner 16, etc.) stored in memory 38. The predetermined degradation threshold may be defined by the user, the manufacturer, league regulations, and the like. Processing circuit 34 is configured to provide an indication of the degree of degradation of the predetermined degradation threshold. The degree of degradation of the predetermined degradation threshold may be in terms of a percent of the predetermined degradation threshold number (e.g., 40% degradation, etc.) and/or a number of remaining uses (e.g., 340 plays, 25 collisions, 95 minutes of time-in-use, etc.) of helmet 10. Processing circuit 34 may be configured to further determine a separate degree of degradation of liner 16 relative to a predetermined degradation threshold at each of a plurality of locations. For example, liner 16 may include a plurality of sections. Some sections of liner 16 may degrade more rapidly than others. As such, by determining a separate degree of degradation at each of the plurality of locations (i.e., sections of liner 16, etc.), an individual section of liner 16 may be deemed substantially degraded and be individually replaced or repaired.

In some embodiments, processing circuit 34, is configured to schedule a future inspection of helmet 10 based on the results of testing by test device 30. This scheduling may be based on the rating (e.g., scheduling more frequent testing in response to a low rating than for a high rating). This scheduling may be based on the test data itself (e.g., compliance data, visual imagery, etc.), and may schedule more frequent testing of some portions of the helmet (e.g., portions with poor compliance, discoloration, etc.) than of others. The schedule may be based on a schedule event reaching a specified threshold value. For example, schedule events may include a time, a time interval, a time-in-use for the helmet, a number of impacts, and a number of uses for the helmet. In an embodiment, threshold values are input to helmet 10 by a person (e.g., a coach, an equipment manager, etc.). In another embodiment, processing circuit 34 specifies the threshold value for one or more schedule events (e.g., specifies that the next testing is due either in 2 months, after 150 more uses of the helmet, or after 300 hours of cumulative usage; whichever occurs first); processing circuit 34 can also reset the threshold values or the scheduling event values after testing. In some embodiments, monitoring of the scheduling events and comparison to their threshold values is performed by a person (e.g., a coach, an equipment manager, etc.). In other embodiments, the monitoring and comparison for one or more of the scheduling events is performed by a controller on helmet 10 and by scheduling sensors 28. Examples of such scheduling sensors include accelerometers, strain sensors, pressure sensors, clock, strap sensors, or the like. For example, the number of uses of helmet 10 may be determined by a strap sensor, determining how many times a helmet strap is connected or disconnected; the time interval between connections and disconnections can be measured and accumulated for time-in-use determination. Other methods of determining when a helmet is in use can be employed; for instance using accelerometers to detect motion indicative of use, using pressure sensors to detect presence of a user's head within the helmet, or the like.

In an embodiment, helmet 10 includes one or more data markings 26 to provide processing circuit 34 with information regarding the helmet's identification, rating, or previous testing information (information such as data from sensor 32, the timing of the test, environmental conditions during testing, etc.). Data marking 26 may comprise text, a barcode, an RFID tag, an image, or other indicia. In some embodiments, information such as the helmet's rating or test data is not directly provided by the data marking, but can be accessed from memory (e.g., a database) located on a remote device and associated with (e.g., addressed by) the helmet's identification provided by data marking 26. In some embodiments, testing device 30 includes a data recorder configured to write data marking 26 onto helmet 10.

As shown in FIG. 4, processing circuit 34 is configured to transmit the results (e.g., rating of helmet 10, degree of degradation of liner 16, etc.) raw test data, timing of the tests, of the testing performed on helmet 10 by test device 30 to at least one of a remote device, shown as remote device 45, user I/O device 40, and helmet 10. The transmission of the results may be done via a wired connection or a wireless communication. The wireless communication to transmit the results may be sent (e.g., via technologies such as Wi-Fi, Bluetooth, radio frequency (RF), infrared (IR), or another suitable wireless communication protocol) from processing circuit 34 and received by remote device 45 (e.g., a remote server, laptop, tablet, smartphone, etc.) and/or helmet 10. The transmission may be sent based on a schedule or an event (e.g., upon the taking or analysis of sensor data, upon a change in rating, etc.). In other embodiments, transmission is performed by an RFID tag (active or passive) upon receipt of a query from remote device 45 (e.g., an RFID reader). The transmission received by remote device 45 notifies an equipment manager, a user, a coach, an official, or any other person deemed necessary or appropriate via a notification (e.g., test data, warning message, degree of degradation, rating, etc.) to take appropriate action (e.g., further inspect helmet 10, repair helmet 10, replace liner 16, etc.).

Referring back to FIG. 2, according to one embodiment, a transmission of the test results (e.g., a helmet rating, etc.) is received by controller 18 of helmet 10. Controller 18 may control at least one of first indicator 20 and second indicator 22 to emit an audible indication (e.g., sound, tone, etc.) and/or visual indication (e.g., flashing light, etc.) or control a change in the profile of helmet 10. The prior mentioned visual and auditory indications provide the user of test device 30 with an indication of the rating (e.g., that helmet 10 is one of suitable for use, not suitable for use, requires maintenance, or requires further inspection). User I/O device 40 may also receive the results via a wired connection from processing circuit 34. The results (e.g., rating, degree of degradation, etc.) may be presented on a visual display (e.g., LCD screen, LED screen, etc.) located on test device 30 for a user to see.

Figure 7:
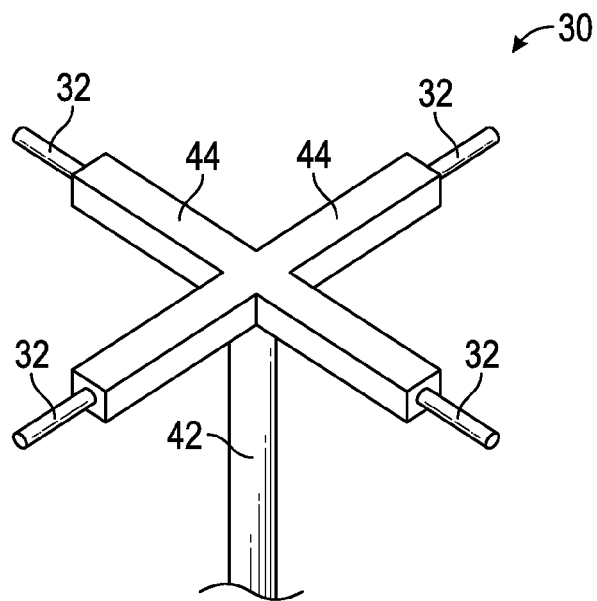
FIG. 7 is a partial perspective view of a test device according to another embodiment.

Referring now to FIG. 7, an alternative embodiment of test device 30 of is shown. As shown in FIG. 7, test device 30 may include a plurality of sensors 32. According to the example embodiment, test device 30 includes four sensors 32. In other embodiments, the number of sensors 32 may be different (e.g., two, three, five, etc.). Test device 30 may selectively position each of the plurality of sensors 32 to engage (e.g., contact, analyze, etc.) a plurality of locations on liner 16 simultaneously. Thereby, test device 30 may acquire compliance data regarding the plurality of locations on liner 16 at one time. The position of the plurality of sensors 32 may be chosen by a user of test device 30 via user I/O device 40 or by processing circuit 34, as described above. Each of the sensors (e.g., sensors 32, etc.) may be configured to move independently, and the sensors may be the same or different types (e.g., such that different types of sensor 32 acquire different types of compliance data for liner 16, etc.).

Figure 8:
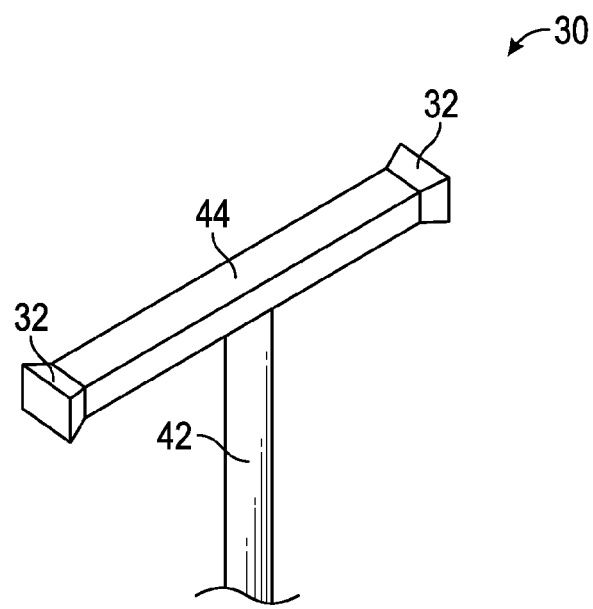
FIG. 8 is a partial perspective view of a test device according to another embodiment.

Referring now to FIG. 8, test device 30 is shown with an alternative sensor 32. As shown in FIG. 8, sensor 32 is configured as a non-contact sensor. For example, sensor 32 may be a camera (e.g., using spectral or polarized light) or other non-contact sensor. In one embodiment, sensor 32 is an optical profilometer. An optical profilometer is a measuring instrument used to measure a surface's profile (e.g., liner 16, etc.). Optical profilometers are non-contact sensors which do not touch a surface and therefore should not be affected by surface wear. In another embodiment, test device 30 may include a sensor that uses laser metrology. In any case, when sensor 32 is configured as a non-contact sensor, test device 30 may be used to inspect changes to liner 16. The changes may include changes in the shape of liner 16 (e.g., dents, bends, folds, etc.), or changes in the appearance of liner 16 (e.g., cracking, discoloration, etc.). Changes in the appearance of liner 16 may indicate aging and/or water damage, which may affect the compliance of liner 16.

Figure 9:
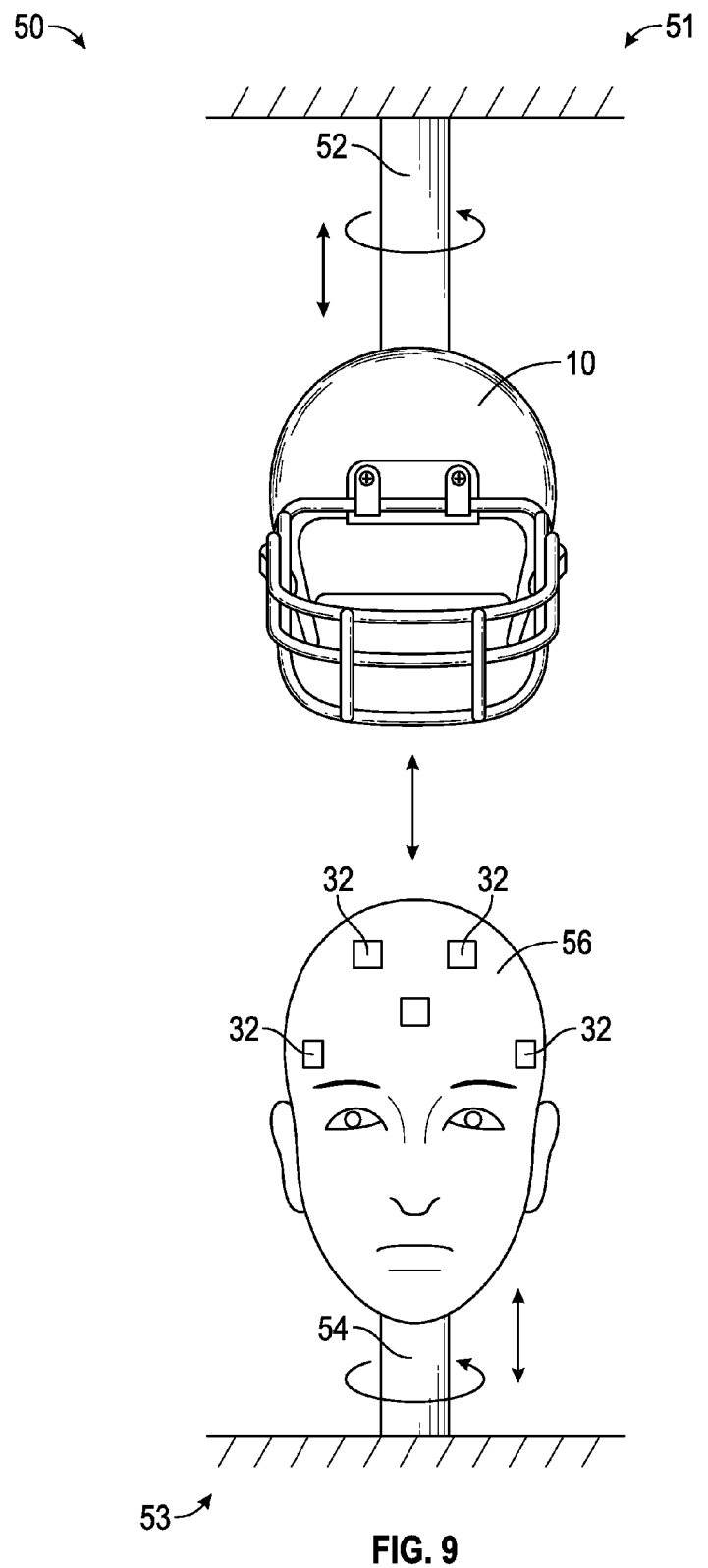
FIG. 9 is an illustration of a test device for testing the helmet of FIG. 1 according to one embodiment.
Figure 10:
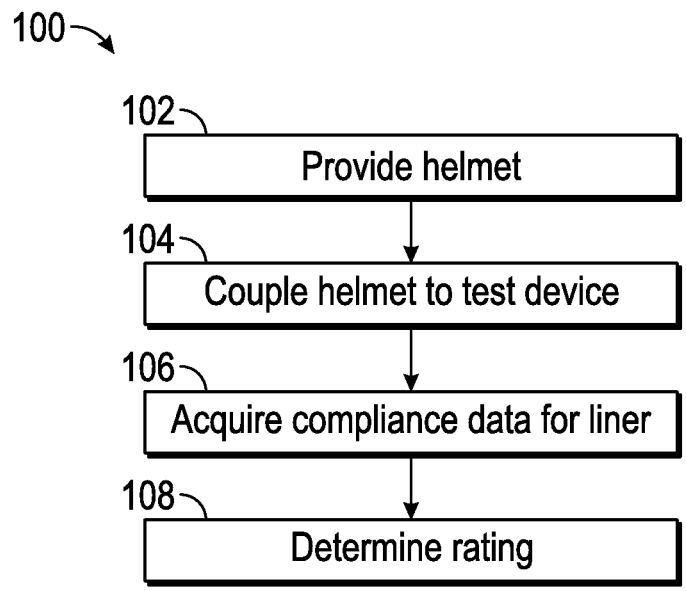
FIG. 10 is a block diagram of a method of testing a helmet according to one embodiment.

Referring now to FIG. 9, an alternative helmet testing apparatus, shown as test device 50, is shown. Test device 50 is configured to test helmet 10 to quantify the angular acceleration or momentum dampening of liner 16. Over time (e.g., a certain number of impacts, plays, time of use, etc.), liner 16 of helmet 10 may begin to degrade from impacts or other degrading forces (e.g., weather, extended use, etc.). Throughout the degradation of liner 16, the performance of helmet 10 to dampen rotational movement of the head of a user relative to helmet 10 from impacts may begin to diminish, putting the user in greater risk of sustaining injuries (e.g., concussions, etc.). Test device 50 may be used to quantify the angular momentum dampening effect of liner 16 of helmet 10 to compare with certain standards or regulations (e.g., of a certain league, of a law, of a manufacturer, etc.) to determine an angular dampening rating for helmet 10.

As shown in FIG. 9, test device 50 includes a first shaft, shown as first shaft 52. A first end (e.g., top end, etc.) of first shaft 52 is rotatably coupled to a first support structure, shown as first support structure 51. A second end (e.g., bottom end, etc.) of first shaft 52 couples helmet 10 to first shaft 52. Test device 50 also includes a second shaft, shown as second shaft 54. A first end (e.g., bottom end, etc.) of second shaft 54 is rotatably coupled to a second support structure, shown as second support structure 53. A mandrel, shown a mannequin head 56, is coupled to a second end (e.g., top end, etc.) of second shaft 54. Mannequin head 56 includes a plurality of sensors, shown as sensors 32, disposed about its structure. Sensors 32 may include contact sensors, non-contact sensors, or a combination of the two. In some embodiments, sensors 32 include accelerometers. Mannequin head 56 may be a general mannequin head or an individually customized mannequin head (e.g., 3D printed replica of the head of the user, etc.). By individually customizing mannequin head 56, the measurements taken by sensors 32, which are described more fully herein, may be substantially more accurate.

By way of example, an actuator, or pair of actuators, may be positioned to rotate at least one of first shaft 52 and second shaft 54. The actuator or pair of actuators may be a linear actuator, a rotary actuator, or still another type of device and may be powered hydraulically, electrically, or still otherwise powered. Both first shaft 52 and second shaft 54 are able to extend towards each other or retract away from one another. For example, at least one of first shaft 52 and second shaft 54 are extended in order to position mannequin head 56 within helmet 10.

Once mannequin head 56 is positioned within helmet 10, the angular momentum dampening testing on liner 16 may begin. The actuator or pair of actuators begin to rotate first shaft 52, second shaft 54, or a combination of the two in order to rotate mannequin head 56 and helmet 10 in unison. Once a rotational target speed (e.g., a speed threshold, etc.) is reached, the rotational actuation of first shaft 52 and second shaft 54 is stopped (e.g., the actuators no longer provide a torque to first shaft 52 or second shaft 54, etc.). Then, either helmet 10 or mannequin head 56 is stopped abruptly (e.g., substantially instantaneous to simulate an impact, to measure relative angular acceleration, etc.) by braking one of first shaft 52 (i.e., helmet 10, etc.) and second shaft 54 (i.e., mannequin head 56, etc.). In one embodiment, the braking is performed on the first shaft 52. Thereby, the angular acceleration (i.e., deceleration, etc.) is known for helmet 10 (e.g., from the rate of change of the angular speed over time for first shaft 52, etc.). The angular acceleration of mannequin head 56 relative to helmet 10 (i.e., liner 16, etc.) is sensed (e.g., measured, quantified, etc.) by sensors 32 during the braking of first shaft 52. From determining the relative angular acceleration of mannequin head 56 to helmet 10, the angular momentum dampening effect of liner 16 is able to be determined. The angular momentum dampening effect of liner 16 is compared with certain standards or regulations (e.g., of a certain league, of the law, of a manufacturer, etc.) to determine an angular dampening rating for helmet 10. The angular dampening rating of liner 16 provides an indication that helmet 10 is one of suitable for use, is not suitable for use, requires maintenance, or requires further inspection (e.g., by an equipment manager, the manufacturer, etc.).

According to an example embodiment, shell 12 of helmet 10 may be inspected for compliance. For example, shell 12 may be inspected for dents, cracks, and/or other features that may reduce the effectiveness of helmet 10 to reduce impact forces to the head of the user or otherwise cause helmet 10 to be substantially compromised. In one embodiment, the compliance of shell 12 may be tested when helmet 10 is positioned on the head of the user (e.g., in-between plays on the sideline, etc.). This substantially prevents the user from having to remove helmet 10 from their head when performing the test. In other embodiments, the testing may be performed after helmet 10 has been removed from the head of the user (e.g., after a game, in-between games, etc.).

Figure 11:
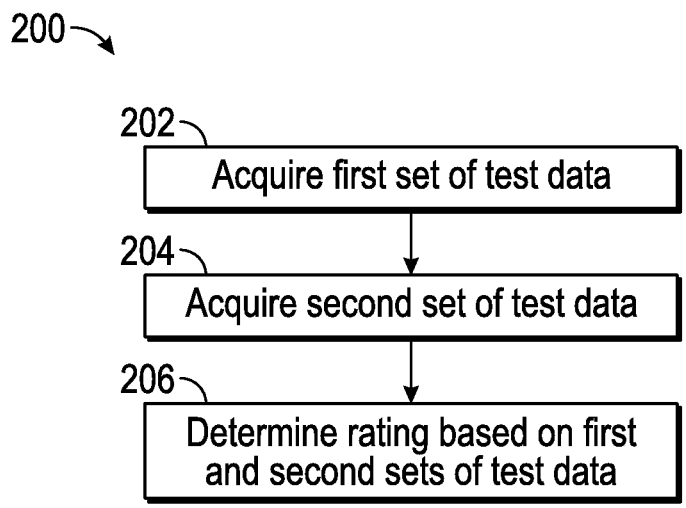
FIG. 11 is a block diagram of a method of testing a helmet based on a first set of test data according to one embodiment.

Referring now to FIG. 11, method 100 of a method of testing a helmet is shown according to an example embodiment. In one example embodiment, method 100 may be implemented with helmet 10 of FIGS. 1-2 and test device 30 of FIGS. 3-4. Accordingly, method 100 may be described in regard to FIGS. 1-4.

At 102, a helmet (e.g., helmet 10, etc.) including a shell with a liner disposed within the shell is provided. In one embodiment, the helmet is new (e.g., never worn, used, etc.) and has never been tested. In other embodiments, the helmet is used (e.g., may have substantial liner degradation, etc.) and is tested periodically based on a schedule (e.g., a time since a previous test, a time-in-use of the helmet, a number of impacts experienced by the helmet, a number of plays the helmet has been in use, etc.). At 104, the helmet is coupled to a test device (e.g., test device 30, test device 50, etc.). For example, helmet 10 may rest on first support member 46 and second support member 48 of test device 30. At 106, compliance data for the liner (e.g., liner 16, etc.) is acquired by a sensor (e.g., sensor 32, etc.). For example, sensor 32 of test device 30 may be selectively positioned to engage a portion of liner 16 in a plurality of locations. As mentioned above, the plurality of locations may be defined by a one-dimensional grid extending along the liner, a two-dimensional grid disposed about the liner, and/or corresponding locations of anatomical features of a user of the helmet. The plurality of locations may be tested in a serial manner (e.g., a single sensor test device, etc.) or simultaneously (e.g., a multi-sensor test device, etc.). In one embodiment, the sensor applies a steady (e.g., linear, etc.) load to determine a linear response of the liner. In other embodiments, the sensor applies a pulsed (e.g., non-linear, etc.) load to determine a non-liner response of the liner.

At 108, a rating for the helmet is determined. In one embodiment, a processing circuit (e.g., processing circuit 34, etc.) determines the rating for the helmet based on the compliance data (e.g., linear response, non-linear response, etc.) and predetermined compliance parameters (e.g., compliance standards, regulations, etc.). In other embodiments, the rating is further based on at least one of a time since a previous test, a time-in-use for the helmet, and a number of uses of the helmet. The rating includes an indication of the helmet being suitable for use, the helmet not being suitable for use, the helmet requiring maintenance, or the helmet requiring further inspection. Once the rating of the helmet is determined, an indication of the rating may be supplied to one or more appropriate people (e.g., a user, a coach, an equipment manager, a doctor, etc.). As mentioned above, the indication may be provided by an audible indication (e.g., via first indicator 20, second indicator 22, etc.), a visual indication (e.g., via first indicator 20, second indicator 22, user I/O device 40, etc.), and/or a transmission of a wireless communication to a remote device (e.g., via controller 18, processing circuit 34, etc.).

Referring now to FIG. 12, method 200 of a method of testing a helmet based on a first set of test data is shown according to an example embodiment. In one example embodiment, method 200 may be implemented with helmet 10 of FIGS. 1-2 and test device 30 of FIGS. 3-4. Accordingly, method 200 may be described in regard to FIGS. 1-4.

At 202, a first set of testing data (e.g., compliance data, an indication of degradation of the liner, etc.) regarding a condition of a liner of a helmet at a first point in time is acquired and stored in a memory (e.g., memory 38, etc.). For example, sensor 32 of test device 30 may be selectively positioned to engage a portion of liner 16 in a plurality of locations. As mentioned above, the plurality of locations may be defined by a one-dimensional grid extending along the liner, a two-dimensional grid disposed about the liner, and/or corresponding locations of anatomical features of a user of the helmet. The plurality of locations may be tested in a serial manner (e.g., a single sensor test device, etc.) or simultaneously (e.g., a multi-sensor test device, etc.). In one embodiment, the sensor applies a steady (e.g., linear, etc.) load to determine a linear response of the liner. In other embodiments, the sensor applies a pulsed (e.g., non-linear, etc.) load to determine a non-liner response of the liner. The acquired compliance data (e.g., the first set of testing data, etc.) may be stored in a memory (e.g., memory 38, etc.) or other storage locations (e.g., external storage, memory, etc.).

Based on a testing schedule, (e.g., a time since a previous test, a time-in-use for the helmet, a number of uses of the helmet, etc.), a second set of testing data regarding the condition of the liner at a second later point in time is acquired (204). In one embodiment, a plurality of locations tested at the second later point in time are selected based on the first set of testing data acquired at the first point in time. In other embodiments, the plurality of locations tested at the second later point in time are selected based a one-dimensional grid extending along the liner, a two-dimensional grid disposed about the liner, and/or corresponding locations of anatomical features of a user of the helmet. The plurality of locations may be tested in a serial manner (e.g., a single sensor test device, etc.) or simultaneously (e.g., a multi-sensor test device, etc.).

At 206, a rating for the helmet based on the first and second sets of testing data is determined regarding the condition of the liner. In some embodiments, the rating is further based on a time since a previous test, a time-in-use for the helmet, and/or a number of uses of the helmet. The rating includes an indication of the helmet being suitable for use, the helmet not being suitable for use, the helmet requiring maintenance, or the helmet requiring further inspection. Once the rating of the helmet is determined, an indication of the rating may be supplied to one or more appropriate people (e.g., a user, a coach, an equipment manager, a doctor, etc.). As mentioned above, the indication may be provided by an audible indication (e.g., via first indicator 20, second indicator 22, etc.), a visual indication (e.g., via first indicator 20, second indicator 22, user I/O device 40, etc.), and/or a transmission of a wireless communication to a remote device (e.g., via controller 18, processing circuit 34, etc.).

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A helmet testing apparatus, comprising:
   a movable member;
   a sensor coupled to the movable member and configured to acquire compliance data regarding a liner disposed within a shell of a helmet, the sensor configured to be removably positioned within an internal head cavity of the helmet to engage with the liner to acquire the compliance data; and
   a processing circuit configured to determine a rating for the helmet based on the compliance data and predetermined compliance parameters for the helmet.

2. The apparatus of claim 1, wherein the rating is further based on at least one of a time since a previous test, a time-in-use for the helmet, and a number of uses of the helmet.

3. The apparatus of claim 1, wherein the sensor is configured to engage the liner at a plurality of locations.

4. The apparatus of claim 3, wherein the plurality of locations are defined by corresponding locations of anatomical features of a user of the helmet.

5. The apparatus of claim 3, wherein the plurality of locations are selected based on previous test data regarding the helmet.

6. The apparatus of claim 5, wherein the previous test data includes an indication of degradation of the liner for at least one of the plurality of locations.

7. The apparatus of claim 1, wherein the processing circuit is configured to schedule a future test of the helmet based on the compliance data.

8. The apparatus of claim 7, wherein the future test is scheduled based on at least one of a time, a time interval, a time-in-use for the helmet, a number of impacts, and a number of uses for the helmet.

9. The apparatus of claim 1, wherein the processing circuit is further configured to determine a degree of degradation of the liner relative to a predetermined degradation threshold.

10. The apparatus of claim 1, wherein the sensor includes a plurality of sensors configured to test a plurality of locations simultaneously.

11. The apparatus of claim 1, wherein the compliance data provides an indication of acceleration dampening provided by the liner.

12. The apparatus of claim 1, wherein the compliance data provides an indication of angular acceleration dampening by the liner.

13. A testing system, comprising:
    a memory configured to store a first set of testing data regarding a condition of a liner of a helmet at a first point in time;
    a sensor configured to acquire a second set of testing data regarding the condition of the liner at a second later point in time; and
    a processing circuit configured to determine a rating for the helmet based on a comparison of the first and second sets of testing data regarding the condition of the liner.

14. The system of claim 13, wherein the first and second sets of testing data provide indications of acceleration dampening of the liner.

15. The system of claim 13, wherein the first and second sets of testing data provide indications of angular acceleration dampening of the liner.

16. The system of claim 13, wherein the sensor includes a plurality of sensors configured to test a plurality of locations simultaneously during at least one of the first point in time and the second later point in time.

17. The system of claim 13, wherein the rating is further based on at least one of a time since a previous test, a time-in-use for the helmet, and a number of uses of the helmet.

18. The system of claim 13, wherein the sensor is configured to engage the liner at a plurality of locations.

19. The system of claim 18, wherein the plurality of locations are defined by corresponding locations of anatomical features of a user of the helmet.

20. The system of claim 18, wherein the plurality of locations tested at the second later point in time are selected based on the first set of testing data acquired at the first point in time regarding the helmet.

21. The system of claim 13, wherein the processing circuit is further configured to determine a degree of degradation of the liner relative to a predetermined degradation threshold.

22. The system of claim 21, wherein the processing circuit is configured to provide an indication of the degree of degradation in terms of a percent of the predetermined degradation threshold.

23. The system of claim 21, wherein the processing circuit is configured to provide an indication of the degree of degradation in terms of a number of remaining uses of the helmet.

24. The system of claim 13, wherein the processing circuit is configured to determine a separate degree of degradation of the liner relative to a predetermined degradation threshold at each of a plurality of locations.

25. A helmet, comprising:
    a shell;
    a liner disposed within the shell; and
    an indicator module configured to provide an indication of a required test inspection time for the helmet;
    wherein the indicator module includes a controller configured to determine the required test inspection time for the helmet based on a comparison of a schedule event to a threshold value for the schedule event, the schedule event comprising at least one of a time, a time since a previous test, a time-in-use of the helmet, and a number of uses of the helmet.

26. The helmet of claim 25, wherein the indication is provided through at least one of a change in profile of the helmet, an audible indication, a visual indication, and a transmission of a wireless communication to a remote device.

27. The helmet of claim 25, wherein the schedule event comprises a number of impacts experienced by the helmet.

28. The helmet of claim 25, further comprising a scheduling sensor comprising at least one of an accelerometer, a strain sensor, a pressure sensor, a clock, and a strap sensor.

29. The helmet of claim 28, wherein the processor is configured to determine the schedule event based on data from the scheduling sensor.

30. The helmet of claim 25, further comprising a sensor configured to measure impact data regarding an impact to the helmet.

31. The helmet of claim 30, wherein the indicator module is configured to provide an indication when the impact data exceeds an impact threshold.

32. The helmet of claim 31, wherein the indication indicates that testing needs to be performed on at least one of the helmet and a user of the helmet.

33. The helmet of claim 25, wherein the required test inspection time is based on acceleration dampening of the liner.

34. The helmet of claim 25, wherein the required test inspection time is based on angular acceleration dampening of the liner.

* * * * *